United States Patent [19]

Silvers

[11] Plant 4,159

[45] Nov. 29, 1977

[54] APPLE TREE

[75] Inventor: William E. Silvers, Zillah, Wash.

[73] Assignees: Claud Callahan; Marjorie McCormick, both of Yakima, Wash.

[21] Appl. No.: 742,529

[22] Filed: Nov. 15, 1976

[51] Int. Cl.[2] ..... A01H 5/03

[52] U.S. Cl. ..... Plt./35

[58] Field of Search ..... Plt./35

*Primary Examiner*—Robert E. Bagwill
*Attorney, Agent, or Firm*—Frank B. Robb

[57] ABSTRACT

There is disclosed an apple variety in which the tree is more dwarf than the parent with many fruit spurs, larger, deeper green, heavier and tougher leaves than "Hi Early" Delicious, long fruit, maturing and ready to harvest two weeks ahead of "Hi Early" and greater sugar test percentage with long-keeping quality.

1 Drawing Figure

The present invention relates to a new and distinct variety of Apple tree which was discovered as a whole tree compact spur sport of the variety known as "Hi Early Red Delicious", an unpatented variety which is a standard non-spur tree in my orchard in Zillah, Wash.

At the time of my discovery, I was growing a large number of trees of the Hi Early variety previously mentioned, and noticed this particular tree when it was in its third growing season and had produced its first crop of fruit; this crop being highly colored.

I discovered this particular tree in a block of Hi Early Red Delicious, in my orchard, and recognized the value of this new sport that matured and was able to be harvested earlier than the parent variety together with the fact that the compact growth of fruiting wood made it even more attractive.

By budding, I prepared a large quantity of seedlings for planting in the same orchard as the parent tree, and periodically top worked the sport in the same orchard from other varieties. Second generation fruit was observed from a tree as being identical to that on the parent tree.

By budding, I have determined and observed and tested succeeding generations and I am convinced that my new sport is definitely distinguished from its parent as well as from other varieties of apple trees of which I am aware, as evidenced by the following unique combination of principal characteristics which are outstanding in the sport:

1. The continuous ability to grow semi-dwarf trees, these being full of fruit spurs and being more compact than the "Starkrimson" Red Delicious U.S. Plant Pat. No. 1,565, which is the standard for comparison; however, it is more spreading than the "Starkrimson".

2. The larger leaves which are deeper green color and heavier and tougher than the parent variety.

3. The bright cherry red striped early color, beautifully long type fruit is also distinguishing; the coloring beginning with a red stripe that finishes into solid cherry red three weeks ahead of the recommended harvest season.

4. The early harvest season, two weeks ahead of the Hi Early parent variety, with the fruit having pure white flesh preharvest compared to other Red Delicious varieties.

5. The long-keeping characteristics which indicate that the variety keeps as well in regular cold storage as other varieties do in controlled atmosphere storage.

6. The flavor of the fruit is more nearly like the varieties of many years ago, being very sweet and distinct in contrast to starchy and bland taste of some of the newer varieties.

7. The very juicy, extra firmness of the fruit with sugar tests on the new variety, higher than Hi Early or other varieties, including "Starking" by 1 to 2 percent S.S. with pressure testing at 18 pounds.

8. The natural dwarf characteristics of the tree, being a compact spur, enables the variety to be grown on seedling roots and still be planted closely, eliminating the need for and expense of propagating on clonal root stock.

9. A comparison of the instant variety with other spur types discloses that one type, "Oregon Spur" is more spreading, matures later, is not as dwarf and does not have white flesh as early. Another spur type "Red Chief" is not as compact a spur nor as dwarf, having heavier striped pattern of color than my new variety, which has a pin stripe and brighter solid red color at harvest.

Asexual reproduction of my new variety through several generations by budding, as performed by me in my orchard at Zillah, Washington, shows that the foregoing characteristics and distinctions come true and are established and transmitted through succeeding propagations.

The accompanying drawing shows branches of a tree of my new variety, indicating the coloring and distinct Delicious shape, with typical foliage and fruit specimens all as depicted in color as nearly true as is reasonably possible to make the same in a color illustration of this character.

The following is a detailed description of my new variety, with color terminology reference being made to the Nickerson Color Fan published by Munsell Color Company, except where general terms of ordinary dictionary significance are applicable:

Locality where grown and observed: Zillah, Wash.

Dates of first and last pickings: About September 2 to September 5, or approximately 123 days from full bloom.

Tree: Semi-drawf; medium vigor; spreading; dense; vase-formed; rapid growing; half hardy; very productive; regular bearer.

*Trunk.*—Stocky; smooth.

*Branches.*—Thick; smooth; much-branched.

*Color.*—Brown; moderate reddish brown 7/5R 3/6.

*Lenticels.*—Numerous; small.

Foliage:

*Leaves.*—Large; long (from about 4½ inches) medium wide (from about 2 inches); ovate; taper-pointed; thick; smooth; Color — Dark green (moderate olive green 5GY 4/3). Margin — Finely serrate. Petiole — Long (about 1¾ inches); slender.

Flowers:

*Dates of first and full bloom.*—About April 23 and April 29 respectively, about midway as compared with other varieties in time of blooming.

*Size.*—Medium.

*Color.*—Pink.

Fruit:

*Maturity when described.*—September 2nd acceptable maturity for market.

*Size.*—Uniform; axial diameter about 3½ inches; transverse diameter about 3¼ inches.

*Form.*—Uniform; symmetrical; regular; oblong; ovate.

*Cavity.*—Symmetrical; acuminate even. Depth — about ½ inch. Breadth — about ½ inch.

*Basin.*—Unsymmetrical; abrupt; wide base; furrowed; angular; pubescent.

*Stem.*—Medium caliper; glabrous. Length — About 1 inch.

*Bracts.*—Missing.

*Calyx.*—Closed; segments persistent, narrowly acute; about ¼ inch long; erect; apex converged from base toward center; outer surface pubescent; inner surface pubescent.

*Eye.*—Small.

*Skin.*—Thick; smooth; glossy; waxed. Dots — Obscure; many; small; circular. Color — Pink. Distribution — Uniform. Ground color — Pink; striped with red and crimson stripes. Bloom — Moderate. Scarfskin — Wanting. General color effect — Solid red with darker stripes 5R 3/7 dark red.

*Flesh.*—Juicy. Color — Very white. Texture — Hard; firm; fine; crisp. Flavor — Mild; sweet; delicate. Aroma — Pronounced. Quality — Best. Core — Medium. Bundle area — Medium sized; symmetrical. Halves of core — Equal. Bundles — Yellowish; conspicuous. Alternate bundle — Reaches tube above stamens. Core lines — Clasping; distinct cross section. Carpellary area — Distinct in cross section; small size. Calyx tube — Pubescent; funnel formed. Stem of funnel — Short. Depth of tube to shoulder — About ¼ inch. Entire depth — About ½ inch. Styles — Present; united; pubescent throughout. Stamens — In one whorl; median. Axillary cavity — Wanting. Seed cells — Open. Cell walls — Distant; thick; tough. Length — About ¾ inch. Breadth — About ¼ inch. Longitudinal section — Narrowly ovate. Surface — Smooth. Cross section — Narrow.

Seeds: eight perfect; two imperfect; usually not more than two in one cell.

*Length.*—¼ inch.

*Breadth.*—About 3/16 inch.

*Form.*—Acute.

*Color.*—Brown 10R ¾ moderate reddish brown.

Use: Market; dessert.

Keeping quality: Good; about 300 days in ordinary storage.

Disease and insect resistance: The tree and fruits are virtually immune to disease such as scab, blight, mildew, measles virus, collar rot, crown gall, canker, rubbery wood and other virus disorders determined from comparison with other varieties grown under the same conditions in the area of Zillah, Wash.

I claim:

1. A new and distinct variety of Apple tree, substantially as herein shown and described, characterized particularly as to novelty by the unique combination of a more dwarf tree with many fruit spurs and larger, deeper green color, heavier and tougher leaves than the variety "Hi Early Delicious", bright cherry red striped early color with exceptionally long fruit, the date of maturity and ability to harvest two weeks ahead of the Hi Early parent variety, the coloring beginning with red striping finishing into solid red 3 weeks ahead of its recommended harvest season, very juicy extra firm fruit with greater sugar test percentage than the Hi Early parent variety, and the ability to keep fruit for much longer periods of time than other varieties, together with its disease resistance.

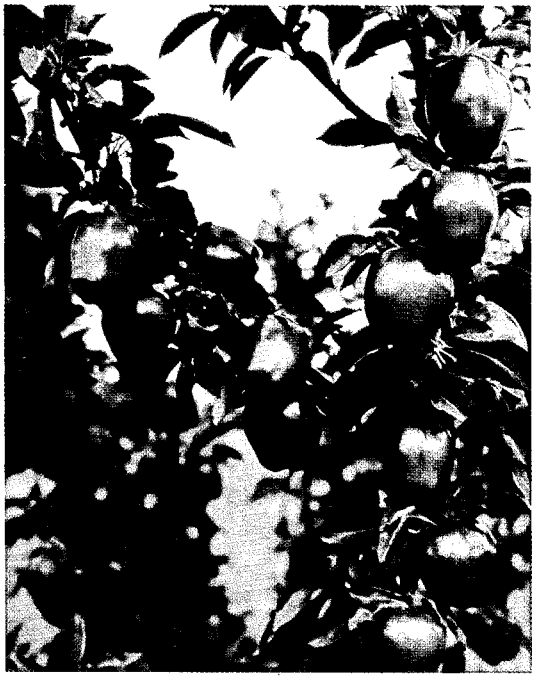

* * * * *